(12) United States Patent
Schuler et al.

(10) Patent No.: US 7,725,176 B2
(45) Date of Patent: *May 25, 2010

(54) METHOD AND SYSTEM FOR REGULATION OF ENDOCRINE AND EXOCRINE GLANDS BY MEANS OF NEURO-ELECTRICAL CODED SIGNALS

(76) Inventors: Eleanor L. Schuler, 2201 Spruce Needle Rd., Rio Rancho, NM (US) 87124; Claude Lee, 465 S. Meadows Pkwy. #20-28, Reno, NV (US) 89521

( * ) Notice: Subject to any disclaimer, the term of this patent is extended or adjusted under 35 U.S.C. 154(b) by 939 days.

This patent is subject to a terminal disclaimer.

(21) Appl. No.: 11/401,734

(22) Filed: Apr. 10, 2006

(65) Prior Publication Data

US 2006/0184205 A1    Aug. 17, 2006

Related U.S. Application Data

(63) Continuation-in-part of application No. 10/889,407, filed on Jul. 12, 2004, now Pat. No. 7,058,446.

(60) Provisional application No. 60/486,089, filed on Jul. 10, 2003.

(51) Int. Cl.
*A61N 1/18* (2006.01)
(52) U.S. Cl. ............................................. 607/2; 607/40
(58) Field of Classification Search ...................... 607/2, 607/40
See application file for complete search history.

(56) References Cited

U.S. PATENT DOCUMENTS

| 5,231,988 | A |  | 8/1993 | Wernicke et al. |
| 6,171,239 | B1 | * | 1/2001 | Humphrey ................... 600/372 |
| 6,775,573 | B2 | * | 8/2004 | Schuler et al. ................. 607/40 |
| 6,826,428 | B1 |  | 11/2004 | Chen et al. |
| 6,853,862 | B1 | * | 2/2005 | Marchal et al. ................ 607/40 |
| 7,058,446 | B2 | * | 6/2006 | Schuler et al. .................. 607/2 |
| 2003/0208242 | A1 | * | 11/2003 | Harel et al. .................... 607/40 |
| 2004/0143296 | A1 | * | 7/2004 | Wang et al. ..................... 607/2 |
| 2005/0153885 | A1 |  | 7/2005 | Yun et al. |
| 2005/0196244 | A1 |  | 9/2005 | Boveja et al. |

FOREIGN PATENT DOCUMENTS

| EP | 199346 | 11/1993 |
| WO | PCT/US00/40301 | 1/2002 |

* cited by examiner

*Primary Examiner*—Carl H Layno
*Assistant Examiner*—Yun Haeng Lee
(74) *Attorney, Agent, or Firm*—Kermit D. Lopez; Luis M. Ortiz; Ortiz & Lopez, PLLC (57) ABSTRACT

A method to regulate the endocrine and exocrine glands generally comprising generating at least one glandular function waveform signal that substantially corresponds to at least one waveform signal that is generated in the body and is operative in the regulation of an endocrine or exocrine gland and transmitting the generated glandular function waveform signal to the subject's nervous system.

40 Claims, 2 Drawing Sheets

METHOD AND SYSTEM FOR REGULATION OF ENDOCRINE AND EXOCRINE GLANDS BY MEANS OF NEURO-ELECTRICAL CODED SIGNALS

CROSS-REFERENCE TO RELATED APPLICATIONS

This application is a continuation-in-part of U.S. application Ser. No. 10/889,407, filed Jul. 12, 2004, now U.S. Pat. No. 7,058,446 which claims the benefit of U.S. Provisional Application No. 60/486,089, filed Jul. 10, 2004.

FIELD OF THE PRESENT INVENTION

The present invention relates generally to medical methods for controlling glandular activity in a mammalian body. More particularly, the invention relates to a method and system for regulating the endocrine and exocrine glands by means of neuro-electrical coded signals.

BACKGROUND OF THE INVENTION

As is well known in the art, bodily homeostasis is the process through which organs, glands and the central, cranial and peripheral nervous system harmoniously function to balance life equilibrium. The process includes, but is not limited to, glandular participation in the regulation of the body temperature, heart rate, respiration, digestion, energy metabolism, immunity and reproduction.

The glandular flow of chemicals or hormones plays an important role in the homeostasis process. There are two principal classes of secretory glands; the "endocrine" glands that secrete directly into the blood stream, and the "exocrine" glands that secrete into ducts in the body.

Endocrine glands include the pituitary, thyroid, adrenal, parathyroid, ovary, testis and part of the pancreas. The endocrine glands also include the placenta, thymus and pineal gland.

Exocrine glands include the mammary glands that secrete milk and the sweat glands, which help cool the body. The exocrine glands also include the sebaceous glands, which lubricate the surface of the skin with an oily substance and the lachrymal glands, which make tears to cleanse and lubricate the eyes.

Another type of exocrine glands are those that provide digestive chemicals, such as saliva from the salivary glands, bile from the liver, and pancreatic juice from the liver; all of which are involved in the digestion of food.

As is also well known in the art, the brain modulates (or controls) the endocrine and exocrine glands via electrical signals (i.e., action potentials or waveform signals), which are transmitted through the nervous system. The nervous system includes two components: the central nervous system, which comprises the brain, brain stem and the spinal cord, and the peripheral nervous system, which generally comprises groups of nerve cells (i.e., neurons) and peripheral nerves that lie outside the brain and spinal cord. The two systems are anatomically separate, but functionally interconnected.

As indicated, the peripheral nervous system is constructed of nerve cells (or neurons) and glial cells (or glia), which support the neurons. Operative neuron units that carry signals from the brain are referred to as "efferent" nerves. "Afferent" nerves are those that carry sensor or status information to the brain and brain stem.

A typical neuron includes four morphologically defined regions: (i) cell body, (ii) dendrites, (iii) axon and (iv) presynaptic terminals. The cell body (soma) is the metabolic center of the cell. The cell body contains the nucleus, which stores the genes of the cell, and the rough and smooth endoplasmic reticulum, which synthesizes the proteins of the cell.

The neuron cell body typically includes two types of outgrowths (or processes); the dendrites and the axon. Most neurons have several dendrites; these branch out in tree-like fashion and serve as the main apparatus for receiving signals from other nerve cells.

The axon is the main conducting unit of the neuron. The axon is capable of conveying electrical signals along distances that range from as short as 0.1 mm to as long as 2 m. Some axons split into several branches, thereby conveying information to different targets.

Near the end of the axon, the axon is divided into fine branches that make contact with other neurons. The point of contact is referred to as a synapse. The cell transmitting a signal is called the presynaptic cell, and the cell receiving the signal is referred to as the postsynaptic cell. Specialized swellings on the axon's branches (i.e., presynaptic terminals) serve as the transmitting site in the presynaptic cell.

Most axons terminate near a postsynaptic neuron's dendrites. However, communication can also occur at the cell body or, less often, at the initial segment or terminal portion of the axon of the postsynaptic cell.

The electrical signals transmitted along the axon to control the endocrine and exocrine glands occur naturally as (i) a burst of neuron activity, i.e., rapid and transient "all-or-none" nerve impulses, or (ii) a continuous pattern of signals followed by a pause, another burst and a final pause of shorter or longer duration, with periods of silence. The amplitude of a signal (or signals) or duration of each pause can be varied to accomplish the required glandular activity.

A "neurosignal" is a composite electrical signal that includes a plurality of nerve impulses (or action potentials) or pattern of signals, and an instruction set for proper gland and organ function. A lachrymal gland (i.e., exocrine gland) neurosignal would thus include an instruction set for commencing secretion of tears to cleanse and lubricate the eyes, the amount and duration of the tears, etc.

Neurosignals or "neuro-electrical coded signals" are thus codes that contain complete sets of information for complete gland and organ function. As set forth in Co-Pending application Ser. No. 11/125,480, filed May 9, 2005, once these neurosignals have been isolated, standardized and transmitted to a subject (or patient), a generated nerve-specific waveform instruction can be employed to regulate the endocrine and exocrine glands and, hence, treat a multitude of disorders associated therewith. The noted disorders include, but are not limited to, abnormal levels of secretion of endogenous insulin, hyperthyroidism, hypothyroidism, Cushing's syndrome, Addison's disease, abnormal levels of testosterone and dry eyes.

Various apparatus, systems and methods have been employed to treat glandular abnormalities. Illustrative is the apparatus and method disclosed in U.S. Pat. No. 5,231,988.

A major drawback associated with the apparatus and method disclosed in the noted patent, as well as most known systems, is that the stimulus signals that are generated and transmitted to a subject are "user determined" and "device determinative" (e.g., implanted electrical stimulator). The noted "stimulus signals" are thus not related to or representative of the signals that are generated in the body and, hence, would not be operative in the direct regulation or modulation of the endocrine or exocrine glands if transmitted thereto.

It would thus be desirable to provide a method and system for regulating the endocrine and exocrine glands that includes means for generating glandular function waveform signals that substantially correspond to the recorded waveform signals (i.e., coded electrical neurosignals) that are generated in the body and are operative in the regulation of the endocrine and/or exocrine glands, and means for transmitting the glandular function waveform signals to the body.

It is therefore an object of the invention to provide a method and system for regulating the endocrine and exocrine glands that includes means for generating glandular function waveform signals that substantially correspond to coded waveform signals that are generated in the body and are operative in the regulation of the endocrine and exocrine glands.

It is another object of the invention to provide a method and system for regulating the endocrine and exocrine glands that includes means for recording waveform signals that are generated in the body and operative in the regulation of the endocrine and exocrine glands.

It is another object of the invention to provide a method and system for regulating at least one endocrine gland that includes processing means adapted to generate a base-line endocrine gland signal that is representative of at least one coded waveform signal that is generated in the body.

It is another object of the invention to provide a method and system for regulating at least one endocrine gland that includes processing means adapted to compare recorded waveform signals to generated baseline endocrine gland signals and generate an endocrine gland waveform signal as a function of the recorded waveform signal.

It is another object of the invention to provide a method and system for regulating at least one exocrine gland that includes processing means adapted to generate a base-line exocrine gland signal that is representative of at least one coded waveform signal that is generated in the body.

It is another object of the invention to provide a method and system for regulating at least one exocrine gland that includes processing means adapted to compare recorded waveform signals to generated baseline exocrine gland signals and generate a exocrine gland waveform signal as a function of the recorded waveform signal.

It is another object of the invention to provide a method and system for regulating at least one endocrine gland that includes means for transmitting endocrine gland waveform signals to the body that substantially correspond to coded waveform signals that are generated in the body and are operative in the regulation of the endocrine gland.

It is another object of the invention to provide a method and system for regulating at least one exocrine gland that includes means for transmitting exocrine gland waveform signals to the body that substantially correspond to coded waveform signals that are generated in the body and are operative in the regulation of the exocrine gland.

It is another object of the present invention to provide a method and system for regulating the endocrine and exocrine glands that includes means for transmitting glandular function waveform signals directly to the nervous system in the body that substantially correspond to coded waveform signals that are generated in the body and are operative in the regulation of the endocrine and/or exocrine gland.

It is another object of the present invention to provide a method and system for regulating the endocrine and exocrine glands that includes means for generating confounding glandular function waveform signals that are adapted to restrict and/or abate secretion of chemicals and/or hormones from endocrine and exocrine glands when transmitted to a subject.

It is another object of the invention to provide a method and system for regulation of the endocrine and exocrine glands that can be readily employed in the treatment of glandular disorders, including, without limitation, diabetes, hyperthyroidism, hypothyroidism, Cushing's syndrome, Addison's disease, abnormal levels of testosterone and estrogen, and dry eyes.

SUMMARY OF THE INVENTION

In accordance with the above objects and those that will be mentioned and will become apparent below, the method for regulating the endocrine and exocrine glands generally comprises (i) generating at least a first glandular function waveform signal that is recognizable by the endocrine and/or exocrine gland as a modulation signal and (ii) transmitting the first glandular function waveform signal to the subject's body to regulate endocrine and/or exocrine gland function.

In a preferred embodiment of the invention, the first glandular function waveform signal substantially corresponds to at least one waveform signal that is generated in the body and is operative in the regulation of an endocrine or exocrine gland.

In one embodiment of the invention, the first glandular function waveform signal includes at least a second glandular function waveform signal that substantially corresponds to at least one waveform signal that is generated in the body and is operative in the regulation of an endocrine or exocrine gland.

In another embodiment of the invention, the method for regulating an endocrine gland generally comprises (i) capturing coded waveform signals that are generated in the body and are operative in the regulation of at least one endocrine gland, (ii) storing the captured waveform signals in a storage medium, the storage medium being adapted to store the components of the captured waveform signals according to the function performed by the waveform signal components, (iii) generating at least a first endocrine gland waveform signal that substantially corresponds to at least one of the captured waveform signals and is operative in the regulation of the endocrine gland, and (iv) transmitting the first endocrine gland waveform signal to the subject's body.

In another embodiment of the invention, the method for regulating an endocrine gland generally comprises (i) capturing a plurality of waveform signals that are generated in a subject's body and are operative in the regulation of at least a first endocrine gland, (ii) generating a base-line endocrine gland signal from the plurality of captured waveform signals, (iii) capturing a target endocrine gland waveform signal from the subject's body that is operative in the regulation of the first endocrine gland, (iv) comparing the base-line endocrine gland signal to the target endocrine gland waveform signal, (v) generating a first endocrine gland waveform signal based on the comparison of the base-line and target endocrine gland waveform signals, and (vi) transmitting the first endocrine gland waveform signal to the subject's body, the first endocrine gland waveform signal being operative in the regulation of the first endocrine gland.

In another embodiment of the invention, the method for regulating an endocrine gland generally comprises (i) generating at least one confounding glandular function waveform signal that is adapted to restrict the secretion of chemicals and/or hormones from the endocrine gland and (ii) transmitting the confounding glandular function waveform signal to the subject's body to regulate the endocrine gland function.

In another embodiment of the invention, the method for regulating an endocrine gland generally comprises (i) generating at least one confounding glandular function waveform signal that is adapted to abate the secretion of chemicals and/or hormones from the endocrine gland and (ii) transmitting the confounding glandular function waveform signal to the subject's body to regulate the endocrine gland function.

In another embodiment of the invention, the method for regulating an exocrine gland generally comprises (i) capturing coded waveform signals that are generated in the body and are operative in the regulation of at least one exocrine gland, (ii) storing the captured waveform signals in a storage medium, the storage medium being adapted to store the components of the captured waveform signals according to the function performed by the waveform signal components, (iii) generating at least a first exocrine gland waveform signal that substantially corresponds to at least one of the captured waveform signals and is operative in the regulation of the exocrine gland, and (iv) transmitting the first exocrine gland waveform signal to the subject's body.

In another embodiment of the invention, the method for regulating an exocrine gland generally comprises (i) capturing a plurality of waveform signals that are generated in a subject's body and are operative in the regulation of at least a first exocrine gland, (ii) generating a base-line exocrine gland signal from the plurality of captured waveform signals, (iii) capturing a target exocrine gland waveform signal from the subject's body that is operative in the regulation of the first exocrine gland, (iv) comparing the base-line exocrine gland signal to the target exocrine gland waveform signal, (v) generating a first exocrine gland waveform signal based on the comparison of the base-line and target exocrine gland waveform signals, and (vi) transmitting the first exocrine gland waveform signal to the subject's body, the first exocrine gland waveform signal being operative in the regulation of the first exocrine gland.

In another embodiment of the invention, the method for regulating an exocrine gland generally comprises (i) generating at least one confounding glandular function waveform signal that is adapted to restrict the secretion of chemicals and/or hormones from an endocrine or exocrine gland and (ii) transmitting the confounding glandular function waveform signal to the subject's body to regulate endocrine or exocrine gland function.

In another embodiment of the invention, the method for regulating an exocrine gland generally comprises (i) generating at least one confounding glandular function waveform signal that is adapted to abate the secretion of chemicals and/or hormones from an endocrine or exocrine gland and (ii) transmitting the confounding glandular function waveform signal to the subject's body to regulate endocrine or exocrine gland function.

In one embodiment of the invention, the step of transmitting the generated waveform signal to the subject's body is accomplished by direct conduction via attachment of an electrode to the receiving nerve or nerve plexus. This requires a surgical intervention to physically attach the electrode to the selected target nerve.

In another embodiment of the invention, the step of transmitting the generated waveform signal to the subject's body is accomplished by direct conduction or transmission through unbroken skin at a selected appropriate zone on the neck, head, abdomen or thorax. Such zone will approximate a position close to the nerve or nerve plexus onto which the signal is to be imposed.

In yet another embodiment of the invention, the step of transmitting the generated waveform signal to the subject's body is accomplished by transposing the waveform signal into a seismic form. The seismic signal is then sent into a region of the head, neck, abdomen or thorax in a manner that allows the appropriate "nerve" to receive and obey the coded instructions of the seismic signal.

The system to regulate the endocrine and exocrine glands in accordance with one embodiment of the invention generally comprises (i) at least a first signal probe adapted to capture coded waveform signals from a subject's body, the waveform signals being representative of waveform signals that are naturally generated in the body and operative in the regulation of the endocrine and exocrine glands, (ii) a processor in communication with the signal probe and adapted to receive the captured waveform signals, the processor being further adapted to generate at least one glandular function waveform signal based on the captured waveform signals, the glandular function waveform signal substantially corresponding to at least one of the captured waveform signals, and (iii) at least a second signal probe adapted to be in communication with the subject's body for transmitting the glandular function waveform signal to the body to regulate the endocrine and/or exocrine glands.

In another embodiment, the processor is further adapted to generate at least one confounding glandular function waveform signal.

Preferably, the processor includes a storage medium adapted to store the captured waveform signals.

In one embodiment, the processor is adapted to extract and store components of the captured waveform signals in the storage means according to the function performed by the signal components.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "a glandular function waveform signal" includes two or more such signals; reference to "a glandular disorder" includes two or more such disorders and the like.

DEFINITIONS

The term "endocrine gland", as used herein, means and includes, an organ or gland in the body that secretes a regulatory substance within the body, e.g., directly into the circulatory system, such as the pituitary and thyroid glands. For purposes herein, the term "endocrine gland" thus includes the "paracine glands". As is well known in the art, the "paracine glands" are located in the digestive tract and act only on local cells.

The term "exocrine gland", as used herein, means and includes a gland that secretes a regulatory substance into and through ducts or canals in the body, which, in most instances, lead to an external surface of the body, such as the sweat and mammary glands.

The term "nervous system", as used herein, means and includes the central nervous system and brain stem, including the spinal cord, medulla oblongata, pons, cerebellum, midbrain, diencephalon and cerebral hemisphere, and the peripheral nervous system, including the neurons and glia.

The term "plexus", as used herein, means and includes a branching or tangle of nerve fibers outside the central nervous system.

The term "ganglion", as used herein, means and includes a group or groups of nerve cell bodies located outside the central nervous system.

The term "waveform signal", as used herein, means and includes a composite electrical signal that is generated in the body and carried by neurons in the body, including neurocodes, neurosignals and components and segments thereof.

The terms "glandular function waveform signal", "endocrine gland waveform signal" and "exocrine gland waveform signal", as used herein, mean and include a generated signal that substantially corresponds to or is representative of a "waveform signal" that is generated in the body and carried by neurons in the body, and is operative in the regulation or modulation of an endocrine or exocrine gland.

The term "confounding glandular function waveform signal", as used herein, means a generated signal that confounds a naturally generated waveform signal and, when transmitted to a subject, restricts and/or abates secretion of chemicals and/or hormones from an endocrine or exocrine gland.

The term "target zone", as used herein, means and includes, without limitation, a region of the body proximal to a portion of the nervous system whereon the application of electrical signals can induce the desired neural control without the direct application (or conduction) of the signals to a target nerve.

The terms "patient" and "subject", as used herein, mean and include humans and animals.

The present invention substantially reduces or eliminates the disadvantages and drawbacks associated with prior art methods and systems for regulating the endocrine and exocrine glands. In one embodiment of the invention, the system for regulating the endocrine and exocrine glands generally comprises means for recording (or capturing) coded neuro-electrical or waveform signals that are generated in the body and are operative in the regulation of the endocrine and/or exocrine glands, means for generating at least one glandular function waveform signal that substantially corresponds to at least one recorded waveform signal, and means for transmitting the generated glandular function waveform signal directly to the subject's body. In a preferred embodiment of the invention, the glandular function waveform signal is transmitted to the subject's nervous system.

As is well known in the art, neuro-electrical signals associated with the endocrine and exocrine glands originate from various regions of the brain. These signals can be captured or collected from the efferent nerves leading to the endocrine and exocrine glands, the afferent nerves leading to the brain or brain stem to modulate glandular output, the cervical spine or neck. The signals can also be collected directly from the endocrine and exocrine glands.

Methods and systems for capturing coded signals from the body, and for storing, processing and transmitting neuro-electrical signals (or coded waveform signals) are set forth in Co-Pending U.S. application Ser. No. 10/000,005, filed Nov. 20, 2001, U.S. application Ser. No. 11/125,480, filed May 9, 2005, and U.S. application Ser. No. 11/147,497, filed Jun. 7, 2005; which are incorporated by reference herein in their entirety.

Figure 1:
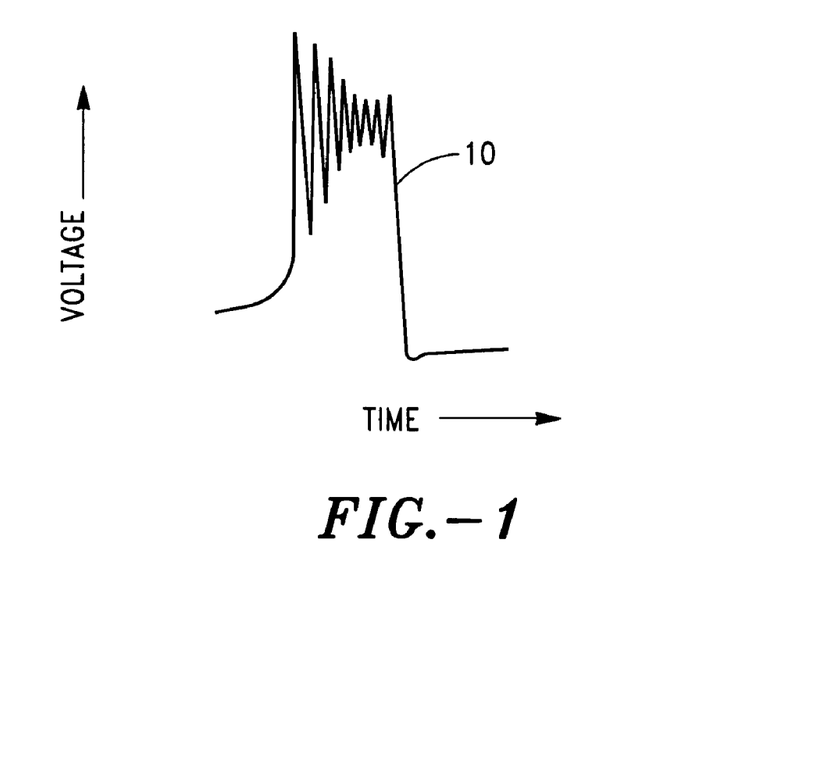
FIG. 1 is an illustration of a waveform signal that is generated in the body and is operative in the regulation of an endocrine gland.

Referring now to FIG. 1, there is shown an illustration of an exemplar waveform signal that is generated in the body and is operative in the regulation of an endocrine gland. More specifically, waveform signal 10 is operative in the control of pancreatic function (i.e., insulin secretion). As is well known in the art, beta pancreatic cells, pituitary somatotrophs and lactotrophs generate the noted plateau-bursting type of waveform signal.

Figure 2:
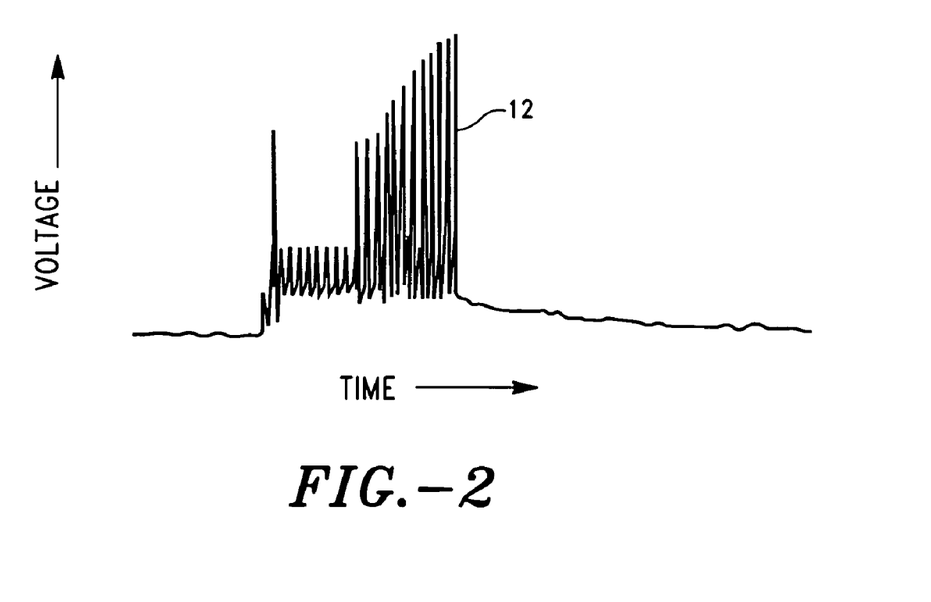
FIG. 2 is an illustration of a waveform signal that is generated in the body and is operative in the regulation of an exocrine gland.

Referring now to FIG. 2, there is shown an illustration of an exemplar waveform signal 12 that is generated in the body and operative in the control of exocrine gland function; in this instance, the ink gland of a marine snail. As will be appreciated by one having ordinary skill in the art, the exocrine gland (and endocrine gland) waveform signals that are generated in the body of an animal are very similar to the exocrine gland (and endocrine gland) waveform signals that are generated in a human body.

Further illustrations of endocrine and exocrine gland waveform signals can be found in Nicholls, et al., *From Neuron to Brain*, (4$^{th}$ ed. 2001); Levitan, et al., *The Neuron, Cell and Molecular Biology* (3$^{rd}$ ed. 2002); Kandel, et al., *Principals of Neural Science* (4$^{th}$ ed. 2000); and P. M. Conn, *Neuroscience in Medicine* (2$^{nd}$ ed. 2003).

Although the methods of the invention set forth below are directed to regulation of the endocrine glands, the methods are equally applicable to regulation of the exocrine glands. The methods thus encompass the regulation of both the endocrine and exocrine glands.

In accordance with one embodiment of the invention, neuro-electrical waveform signals that are generated in the body and are operative in the regulation of at least one endocrine gland are captured and transmitted to a processor or control module. Preferably, the control module includes storage means adapted to store the captured signals. In a preferred embodiment, the control module is further adapted to store the components of the captured signals (that are extracted by the processor) in the storage means according to the function performed by the signal components.

According to the invention, the stored signals can subsequently be employed to establish at least one base line endocrine gland signal. The module can then be programmed to compare the endocrine gland signals (and components thereof) that are subsequently captured from a subject and, as discussed below, generate at least one endocrine gland waveform signal or modified base-line signal for transmission to the subject.

The captured neuro-electrical signals are then processed by known means and, in one embodiment, an endocrine gland waveform signal that is representative of or substantially similar to at least one captured neuro-electrical signal and is operative in the regulation of at least one endocrine gland (i.e., recognized by the brain or an endocrine gland as a modulation signal) is generated by the control module.

In an alternative embodiment of the invention, at least one endocrine gland waveform signal that is representative of or substantially similar to at least one captured neuro-electrical signal and is operative in the regulation of at least one endocrine gland is directly generated by the control module.

As will be appreciated by one having ordinary skill in the art, since the generated endocrine gland waveform signal is substantially similar to or representative of a neuro-electrical waveform signal that is naturally generated in the body, the generated endocrine waveform signal would induce glandular activity that is similar to the glandular activity that is induced by a naturally generated waveform signal. The noted glandular activity would primarily comprise the secretion of chemicals and/or hormones from the gland.

In another embodiment of the invention, at least one confounding glandular function waveform signal is directly generated by the control module. In one embodiment, the confounding glandular function waveform signal is adapted to restrict the secretion of chemicals and/or hormones from the endocrine gland. In another embodiment, the confounding glandular function waveform signal is adapted to abate the secretion of chemicals and/or hormones from the endocrine gland.

According to the invention, the confounding glandular function waveform signal can comprise various forms and can be adapted to modulate glandular function in numerous ways. By way of example, in one envisioned embodiment of the invention, at least one portion of the confounding glandular function waveform signal comprises a substantially negative mirror image of the naturally generated waveform signal, whereby a portion of the naturally generated waveform signal is modified, e.g., amplitude of the signal, enhanced or delayed period of silence, delayed on-set of signal, etc.

In another envisioned embodiment of the invention, the confounding glandular function waveform signal is adapted to substantially abate the effectiveness of the naturally generated waveform signal. By way of example, in the case of an abnormally high secretion of a substance from an endocrine gland, e.g., polysialia, the confounding glandular function waveform signal would be adapted to completely abate the secretion for a predetermined period of time.

The generated endocrine gland waveform signal (and/or confounding glandular function waveform signal) is similarly preferably stored in the storage means of the control module.

Details of a suitable processor and control module are set forth in Co-Pending U.S. application Ser. No. 11/147,497, filed Jun. 7, 2005; which is incorporated herein in its entirety.

According to the invention, the generated endocrine gland waveform signal can include one or more additional signals (constructed or naturally occurring), such as a supplemental modulation or stimulus signal. Thus, in some embodiments of the invention, (discussed in detail below) the generated endocrine gland waveform signal includes at least one waveform signal that substantially corresponds to a waveform signal that is generated in a subject's body and a supplemental signal.

To regulate a target endocrine gland, the generated endocrine gland waveform signal (or confounding glandular function waveform signal) is accessed from the storage means and transmitted to the subject via a transmitter (or probe).

According to the invention, the applied voltage of the endocrine gland waveform signal (or confounding glandular function waveform signal) can be up to 20 volts to allow for voltage loss during the transmission of the signals. Preferably, current is maintained to less than 2 amp output.

Direct conduction into the nerves via electrodes connected directly to such nerves preferably have outputs less than 3 volts and current less than one tenth of an amp.

Figure 3:
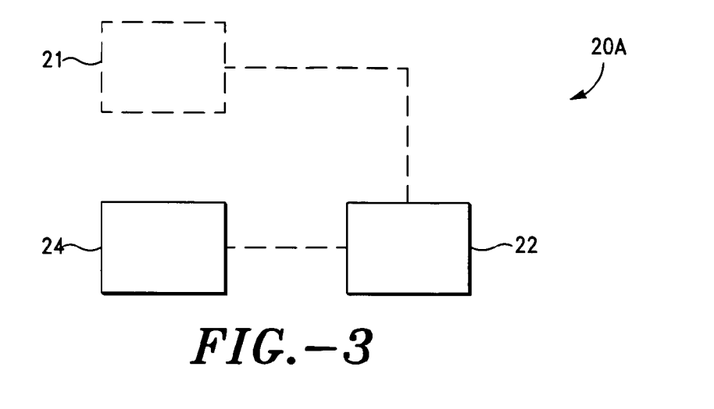
FIG. 3 is a schematic illustration of one embodiment of a glandular activity control system, according to the invention.

Referring now to FIG. 3, there is shown a schematic illustration of one embodiment of a glandular activity control system 20A of the invention. As illustrated in FIG. 3, the control system 20A includes a control module 22, which is adapted to receive neuro-electrical coded signals or "waveform signals" from a signal sensor (shown in phantom and designated 21) that is in communication with a subject, and at least one treatment member 24.

The treatment member 24 is adapted to communicate with the body and receives the generated waveform signal (i.e. glandular function waveform signal or endocrine gland waveform signal or exocrine gland waveform signal (or confounding glandular function waveform signal) from the control module 22. According to the invention, the treatment member 24 can comprise an electrode, antenna, a seismic transducer, or any other suitable form of conduction attachment for transmitting waveform signals that regulate or operate the endocrine and exocrine glands in humans and/or animals.

The treatment member 24 can be attached to appropriate nerves via a surgical process. Such surgery can, for example, be accomplished with "key-hole" entrance in a thoracic-stereo-scope procedure. If necessary, a more expansive thoracotomy approach can be employed for more proper placement of the treatment member 24.

As illustrated in FIG. 3, the control module 22 and treatment member 24 can be entirely separate elements, which allows system 20A to be operated remotely. According to the invention, the control module 22 can be unique, i.e., tailored to a specific operation and/or subject, or can comprise a conventional device.

Figure 4:
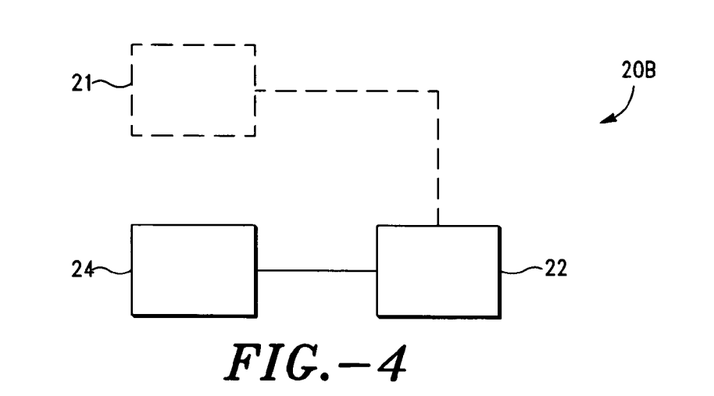
FIG. 4 is a schematic illustration of another embodiment of a glandular activity control system, according to the invention.

Referring now to FIG. 4, there is shown a further embodiment of a glandular activity control system 20B of the invention. As illustrated in FIG. 4, the system 20B is similar to system 20A shown in FIG. 3. However, in this embodiment, the control module 22 and treatment member 24 are connected.

Figure 5:
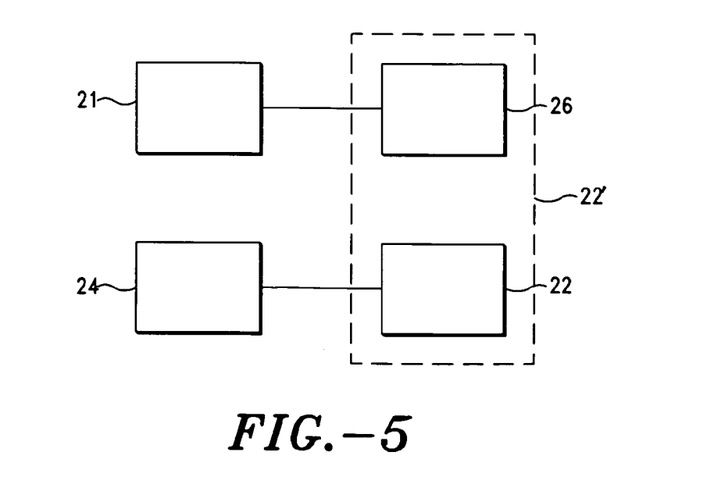
FIG. 5 is a schematic illustration of yet another embodiment of a glandular activity control system, according to the invention.

Referring now to FIG. 5, there is shown yet another embodiment of a glandular activity control system 20C of the invention. As illustrated in FIG. 5, the control system 20C similarly includes a control module 22 and a treatment member 24. The system 20C further includes at least one signal sensor 21.

The system 20C also includes a processing module (or computer) 26. According to the invention, the processing module 26 can be a separate component or can be a subsystem of a control module 22', as shown in phantom.

As indicated above, the processing module (or control module) preferably includes storage means adapted to store the captured waveform signals and the aforementioned generated waveform signals. In a preferred embodiment, the processing module 26 is further adapted to extract and store the components of the captured waveform signals in the storage means according to the function performed by the signal components.

According to the invention, in one embodiment of the invention, the method for regulating an endocrine gland in a subject includes the following steps: (i) generating at least a first endocrine gland waveform signal that is recognizable by the endocrine gland as a modulation signal, and (ii) transmitting the first endocrine gland waveform signal to the subject's body.

In a preferred embodiment, the first endocrine gland waveform signal substantially corresponds to at least one waveform signal that is generated in the body and is operative in the regulation of the endocrine gland.

In an alternative embodiment of the invention, the first endocrine gland waveform signal includes at least a second endocrine gland waveform signal that substantially corresponds to at least one waveform signal that is generated in the body and is operative in the regulation of the endocrine gland.

In another embodiment of the invention, the method for regulating an endocrine gland generally comprises (i) capturing a plurality of coded waveform signals that are generated in the body and are operative in the regulation of at least one endocrine gland, (ii) generating at least a first endocrine gland waveform signal that substantially corresponds to at least one of the captured waveform signals, and (iii) transmitting the first endocrine gland waveform signal to the subject's body.

In another embodiment of the invention, the method for regulating an endocrine gland generally comprises (i) capturing a plurality of coded waveform signals that are generated in the body and are operative in the regulation of at least one endocrine gland, (ii) storing the captured waveform signals in a storage medium, the storage medium being adapted to store the components of the captured waveform signals according to the function performed by the signal components, (iii) generating at least a first endocrine gland waveform signal that substantially corresponds to at least one of the captured waveform signals, and (iv) transmitting the first endocrine gland waveform signal to the subject's body.

In another embodiment of the invention, the method for regulating an endocrine gland generally comprises (i) capturing a plurality of waveform signals that are generated in a subject's body and are operative in the regulation of at least a first endocrine gland, (ii) generating a base-line endocrine gland signal from the plurality of captured waveform signals, (iii) capturing a target endocrine gland waveform signal from the subject's body that is operative in the regulation of the first endocrine gland, (iv) comparing the base-line endocrine gland signal to the target endocrine gland waveform signal, (v) generating a first endocrine gland waveform signal based on the comparison of the base-line and target endocrine gland waveform signals, and (vi) transmitting the first endocrine gland waveform signal to the subject's body, the first endocrine gland waveform signal being operative in the regulation of the first endocrine gland.

In another embodiment of the invention, the method for regulating an endocrine gland generally comprises (i) generating at least one confounding glandular function waveform signal that is adapted to restrict the secretion of at least one regulatory substance from an endocrine gland and (ii) transmitting the confounding glandular function waveform signal to the subject's body to regulate the endocrine gland.

In another embodiment of the invention, the method for regulating an endocrine gland generally comprises (i) generating at least one confounding glandular function waveform signal that is adapted to abate the secretion of at least one regulatory substance from an endocrine gland and (ii) transmitting the confounding glandular function waveform signal to the subject's body to regulate the endocrine gland.

According to the invention, in one embodiment of the invention, the method for regulating an exocrine gland in a subject includes the following steps: (i) generating at least a first exocrine gland waveform signal that is recognizable by the exocrine gland as a modulation signal, and (ii) transmitting the first exocrine gland waveform signal to the subject's body.

In a preferred embodiment, the first exocrine gland waveform signal substantially corresponds to at least one waveform signal that is generated in the body and is operative in the regulation of the exocrine gland.

In an alternative embodiment of the invention, the first exocrine gland waveform signal includes at least a second exocrine gland waveform signal that substantially corresponds to at least one waveform signal that is generated in the body and is operative in the regulation of the exocrine gland.

In another embodiment of the invention, the method for regulating an exocrine gland generally comprises (i) capturing a plurality of coded waveform signals that are generated in the body and are operative in the regulation of at least one exocrine gland, (ii) generating at least a first exocrine gland waveform signal that substantially corresponds to at least one of the captured waveform signals, and (iii) transmitting the first exocrine gland waveform signal to the subject's body.

In another embodiment of the invention, the method for regulating an exocrine gland generally comprises (i) capturing a plurality of coded waveform signals that are generated in the body and are operative in the regulation of at least one exocrine gland, (ii) storing the captured waveform signals in a storage medium, the storage medium being adapted to store the components of the captured waveform signals according to the function performed by the signal components, (iii) generating at least a first exocrine gland waveform signal that substantially corresponds to at least one of the captured waveform signals, and (iv) transmitting the first exocrine gland waveform signal to the subject's body.

In another embodiment of the invention, the method for regulating an exocrine gland generally comprises (i) capturing a plurality of waveform signals that are generated in a subject's body and are operative in the regulation of at least a first exocrine gland, (ii) generating a base-line exocrine gland signal from the plurality of captured waveform signals, (iii) capturing a target exocrine gland waveform signal from the subject's body that is operative in the regulation of the first exocrine gland, (iv) comparing the base-line exocrine gland signal to the target exocrine gland waveform signal, (v) generating a first exocrine gland waveform signal based on the comparison of the base-line and target exocrine gland waveform signals, and (vi) transmitting the first exocrine gland waveform signal to the subject's body, the first exocrine gland waveform signal being operative in the regulation of the first exocrine gland.

In another embodiment of the invention, the method for regulating an exocrine gland generally comprises (i) generating at least one confounding glandular function waveform signal that is adapted to restrict the secretion of at least one regulatory substance from the exocrine gland and (ii) transmitting the confounding glandular function waveform signal to the subject's body to regulate the exocrine gland.

In another embodiment of the invention, the method for regulating an exocrine gland generally comprises (i) generating at least one confounding glandular function waveform signal that is adapted to abate the secretion of at least one regulatory substance from the exocrine gland and (ii) transmitting the confounding glandular function waveform signal to the subject's body to regulate the exocrine gland.

According to the invention, the control of an endocrine and exocrine gland can, in some instances, require sending the generated waveform signals into one or more nerves, including up to ten nerves simultaneously.

The generated waveform signals can also be adjusted (or modulated), if necessary, prior to transmission to the subject.

EXAMPLES

The following examples are given to enable those skilled in the art to more clearly understand and practice the present invention. They should not be considered as limiting the scope of the invention, but merely as being illustrated as representative thereof.

Example 1

A subject is presented that has been diagnosed with hyperhydrosis (i.e., excess sweating). The subject is prescribed sweat gland regulation via a glandular activity control system of the invention. At least one confounding exocrine gland waveform signal is generated by the control module. The generated confounding exocrine gland waveform signal is then directly transmitted to the subject's body nervous system via a signal transmitter, whereby the subject's sweat glands are modulated or controlled.

Example 2

A subject is presented that has been diagnosed with xerophthalmia (i.e. decreased production of tears). The subject is prescribed lacrimal gland regulation via a glandular activity control system of the invention. At least a first exocrine gland waveform signal that substantially corresponds to a waveform signal that is generated in the body is generated by the control module. The generated exocrine gland waveform signal is then directly transmitted to the subject's body nervous system via a signal transmitter, whereby the subject's lacrimal glands are modulated or controlled.

As will be appreciated by one having ordinary skill in the art, the present invention has utility in a multitude of medical applications. Among the medical applications are the treatment of the following disorders:

Xerophthalmia (i.e. decreased production of tears)
Lacrimation (i.e. excess tearing of eyes)
Xerostomia (i.e. decreased production of saliva)
Polysialia (i.e. excessive salivation)
Abnormal level of pancreatic juice secretion
Sjogren's syndrome (i.e. extreme dryness of mouth and eyes)
Diabetes (i.e. abnormal carbohydrate metabolism)
Cushing disease (i.e. hypercortisolism)
Addison's disease (i.e. adrenocortical insufficiency)
Hypothyroidism (i.e. thyroid hormone deficiency)
Hypopituitarism (i.e. thyroid hormone deficiency)
Hyperhidrosis (i.e. excessive perspiration)
Hyperthyroidism (i.e. hypermetabolism)

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for regulating an endocrine gland in a subject, comprising the steps of:
    generating at least a first endocrine gland waveform signal that substantially corresponds to at least one waveform signal that is generated in the body and is operative in the regulation of said endocrine gland; and
    transmitting said first endocrine gland waveform signal to said subject's nervous system.

2. The method of claim 1, wherein said subject comprises a human.

3. The method of claim 1, wherein said subject comprises an animal.

4. A method for regulating an endocrine gland in a subject, comprising the steps of:
    capturing a plurality of waveform signals that are generated in said subject's body, said plurality of waveform signals being operative in the regulation of said endocrine gland;
    generating at least a first endocrine gland waveform signal that substantially corresponds to at least one of said captured waveform signals and is operative in the regulation of said endocrine gland; and
    transmitting said first endocrine gland waveform signal to said subject's nervous system.

5. The method of claim 4, wherein said first endocrine gland waveform signal includes at least one additional modulation signal.

6. A method for regulating an endocrine gland in a subject, comprising the steps of:
    capturing a plurality of waveform signals that are generated in said subject's body, said plurality of waveform signals being operative in the regulation of said endocrine gland;
    storing said captured plurality of waveform signals in a storage medium;
    generating an endocrine gland signal based on said captured plurality of waveform signals, said endocrine gland signal including at least one endocrine gland waveform signal that substantially corresponds to at least one of said captured plurality of waveform signals; and
    transmitting said endocrine gland signal to said subject's nervous system.

7. A method for regulating an endocrine gland in a subject, comprising the steps of:
    capturing a first plurality of waveform signals that are generated in said subject's body, said first plurality of waveform signals being operative in the regulation of said endocrine gland;
    generating a base-line endocrine gland signal from said first plurality of waveform signals;
    capturing a second plurality of waveform signals generated in said subject's body, said second plurality of waveform signals including at least a second waveform signal that is operative in the regulation of said endocrine gland;
    comparing said base-line endocrine gland signal to said second waveform signal;
    generating a first endocrine gland waveform signal based on said comparison of said base-line endocrine gland signal and said second waveform signal;
    transmitting said first endocrine gland waveform signal to said subject's body, said first endocrine gland waveform signal being operative in the regulation of said endocrine gland.

8. The method of claim 7, wherein said base-line endocrine gland signal substantially corresponds to at least one of said first plurality of waveform signals.

9. The method of claim 7, wherein said first endocrine gland waveform signal substantially corresponds to at least one of said first and second plurality of waveform signals.

10. The method of claim 7, wherein said first endocrine gland waveform includes at least one additional modulation signal.

11. The method of claim 7, wherein said first endocrine gland waveform signal substantially corresponds to said second waveform signal.

12. The method of claim 7, wherein said first endocrine gland waveform signal substantially corresponds to said base-line endocrine gland signal.

13. The method of claim 7, wherein said subject comprises a human.

14. The method of claim 7, wherein said subject comprises an animal.

15. A method for regulating an exocrine gland in a subject, comprising the steps of:
   generating at least a first exocrine gland waveform signal that substantially corresponds to at least one waveform signal that is generated in the body and is operative in the regulation of said exocrine gland; and
   transmitting said first exocrine gland waveform signal to said subject's nervous system.

16. The method of claim 15, wherein said subject comprises a human.

17. The method of claim 15, wherein said subject comprises an animal.

18. A method for regulating an exocrine gland in a subject, comprising the steps of:
   capturing a plurality of waveform signals that are generated in said subject's body, said plurality of waveform signals being operative in the regulation of said exocrine gland;
   generating at least a first exocrine gland waveform signal that substantially corresponds to at least one of said captured waveform signals and is operative in the regulation of said exocrine gland; and
   transmitting said first exocrine gland waveform signal to said subject's nervous system.

19. The method of claim 18, wherein said first exocrine gland waveform signal includes at least one additional signal.

20. A method for regulating an exocrine gland in a subject, comprising the steps of:
   capturing a plurality of waveform signals that are generated in said subject's body, said plurality of waveform signals being operative in the regulation of said exocrine gland;
   storing said captured plurality of waveform signals in a storage medium;
   generating an exocrine gland signal based on said captured plurality of waveform signals, said exocrine gland signal including at least one exocrine gland waveform signal that substantially corresponds to at least one of said captured plurality of waveform signals; and
   transmitting said exocrine gland signal to said subject's nervous system.

21. A method for regulating an exocrine gland in a subject, comprising the steps of:
   capturing a first plurality of waveform signals generated in said subject's body, said first plurality of waveform signals being operative in the regulation of said exocrine gland;
   generating a base-line exocrine gland signal from said first plurality of waveform signals;
   capturing a second plurality of waveform signals that are generated in said subject's body, said second plurality of waveform signals including at least a second waveform signal that is operative in the regulation of said exocrine gland;
   comparing said base-line exocrine gland signal to said second waveform signal;
   generating a first exocrine gland waveform signal based on said comparison of said base-line exocrine gland signal and said second waveform signal;
   transmitting said first exocrine gland waveform signal to said subject's body, said first exocrine gland waveform signal being operative in the regulation of said exocrine gland.

22. The method of claim 21, wherein said base-line exocrine gland signal substantially corresponds to at least one of said first plurality of waveform signals.

23. The method of claim 21, wherein said first exocrine gland waveform signal substantially corresponds to at least one of said first and second plurality of waveform signals.

24. The method of claim 21, wherein said first exocrine gland waveform signal includes at least one additional modulation signal.

25. The method of claim 21, wherein said first exocrine gland waveform signal substantially corresponds to said second waveform signal.

26. The method of claim 21, wherein said first exocrine gland waveform signal substantially corresponds to said base-line exocrine gland signal.

27. The method of claim 21, wherein said subject comprises a human.

28. The method of claim 21, wherein said subject comprises an animal.

29. A system for regulating the endocrine and exocrine glands, comprising:
   at least a first signal probe adapted to capture waveform signals from a subject's body;
   a processor in communication with said signal probe and adapted to receive said waveform signals, said processor being further adapted to generate at least one glandular function waveform signal based on said captured waveform signals, said glandular function waveform signal substantially corresponding to at least one of the captured waveform signals; and
   at least a second signal probe adapted to be in communication with said subject's body for transmitting said glandular function waveform signal to said subject's nervous system.

30. The system of claim 29, wherein said processor is further adapted to generate at least one confounding glandular function waveform signal.

31. A method for regulating an endocrine gland in a subject, comprising the steps of:
   generating at least at least one confounding glandular function waveform signal; and
   transmitting said confounding glandular function waveform signal to said subject's nervous system to modulate said endocrine gland.

32. The method of claim 31, wherein said confounding glandular function waveform signal is adapted to restrict secretion of at least one regulatory substance from said endocrine gland.

33. The method of claim 31, wherein said confounding glandular function waveform signal is adapted to abate secretion of at least one regulatory substance from said endocrine gland.

34. A method for regulating an exocrine gland in a subject, comprising the steps of:
   generating at least at least one confounding glandular function waveform signal; and
   transmitting said confounding glandular function waveform signal to said subject's nervous system to modulate said exocrine gland.

35. The method of claim 34, wherein said confounding glandular function waveform signal is adapted to restrict secretion of at least one regulatory substance from said exocrine gland.

36. The method of claim 34, wherein said confounding glandular function waveform signal is adapted to abate secretion of at least one regulatory substance from said exocrine gland.

37. A method for treating a glandular disorder in a subject, comprising the steps of:
   generating a glandular waveform signal that substantially corresponds to at least one waveform signal that is generated in the body; and
   transmitting said glandular waveform signal to said subject's nervous system to treat said glandular disorder.

38. The method of claim 37, wherein said glandular disorder is selected from the group consisting of xerophthalmia, xerostomia, Sjogren's syndrome, diabetes, Addison's disease, hypothyroidism and hypopituitarism.

39. A method for treating a glandular disorder in a subject, comprising the steps of:
   generating a confounding glandular waveform signal; and
   transmitting said confounding glandular waveform signal to said subject's nervous system to treat said glandular disorder.

40. The method of claim 39, wherein said glandular disorder is selected from the group consisting of lacrimation, polysialia, diabetes, Cushing disease, hyperhidrosis and hyperthyroidism.

\* \* \* \* \*